United States Patent [19]
Yabutani et al.

[11] 4,329,479
[45] May 11, 1982

[54] PROCESS FOR PRODUCING 1,3-DITHIOL-2-YLIDENE MALONIC ACID DIALKYL ESTERS

[75] Inventors: Kunihiro Yabutani, Neyagawa; Hisanori Matsui, Nishinomiya; Hiroshi Tanaka, Neyagawa; Hitoshi Kurono, Toyonaka, all of Japan

[73] Assignee: Nihon Nohyaku Co., Ltd., Tokyo, Japan

[21] Appl. No.: 252,003

[22] Filed: Apr. 7, 1981

[51] Int. Cl.³ ............................................ C07D 339/06
[52] U.S. Cl. ...................................................... 549/39
[58] Field of Search ........................................ 549/39

[56] References Cited
U.S. PATENT DOCUMENTS
4,035,387 7/1977 Taninaka et al. ...................... 549/39

Primary Examiner—Henry R. Jiles
Assistant Examiner—Bernard Dentz
Attorney, Agent, or Firm—Cushman, Darby & Cushman

[57] ABSTRACT

A 1,3-dithiol-2-ylidene malonic acid dialkyl ester chich was known as useful agricultural or horticultural fungicide and also as therapeutic agent for treating hepatic diseases can be prepared by a new process which comprises reacting a dialkyloxycarbonylketene dimercaptide with a 1,1-dihalogenoethylene.

7 Claims, No Drawings

PROCESS FOR PRODUCING 1,3-DITHIOL-2-YLIDENE MALONIC ACID DIALKYL ESTERS

This invention relates a process for producing 1,3-dithiol-2-ylidene malonic acid dialkyl esters. They are known compounds useful as agricultural or horticultural fungicide and also as therapeutic agents for treating hepatic diseases.

Referring to the process for synthesizing the 1,3-dithiol-2-ylidene malonic acid dialkyl esters by use of malonic ester derivatives as one of the starting materials, for example, the following processes have been disclosed:

(1) Dehydration of corresponding 4-hydroxy-1,3-dithiolan-2-ylidene malonic esters [Japanese patent application Laid-open No. 48667 (1976)]:

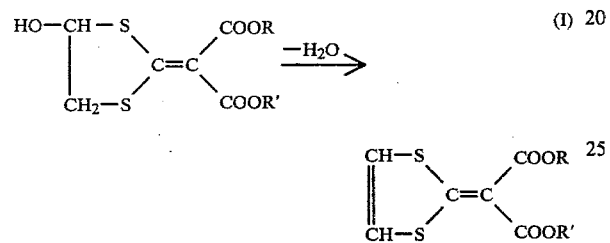

In this equation, R and R' are the same or different and each represents lower alkyl. The same definitions apply hereinafter.

(2) Reaction of corresponding dialkyloxycarbonylketene dimercaptides with a cis-1,2-dihalogenoethylene in an aprotic polar solvent [Japanese patent application Laid-open No. 63085 (1979)].

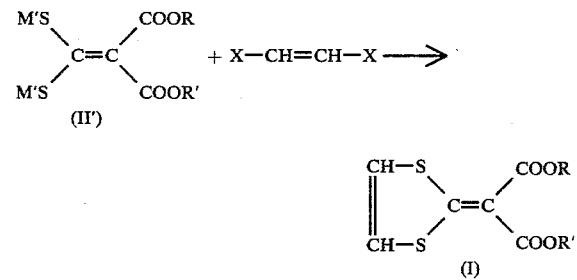

In this equation, M' and X represent alkali metal and halogen, respectively.

In process (1), the starting compounds 4-hydroxy-1,3-dithiolan derivatives are required to synthesize, from substituted ketene mercaptides represented by formula (II'), which are the starting materials of process (2). Therefore, process (1) has the disadvantage that the overall manufacturing process is longer as compared with process (2). Meanwhile, any 1,2-cis-dihalogenoethylene used in process (2) is at present not commercially available as an industrial raw material. Hence, it must be specially manufactured and then would be expensive. Moreover, this compound is difficult to obtain in a purified form and involves the problem of isomerization. Thus, both the prior arts admit of improvements in technical and economical aspects.

Recently, the present inventors have found that dialkyloxycarbonylketene dimercaptides, which can be obtained by the reaction of dialkyl malonates with carbon disulfide, react with a 1,1-dihalogenoethylene to accomplish ring closure, thus giving 1,3-dithiol-2-ylidene malonates.

This reaction can be schematically represented as follows:

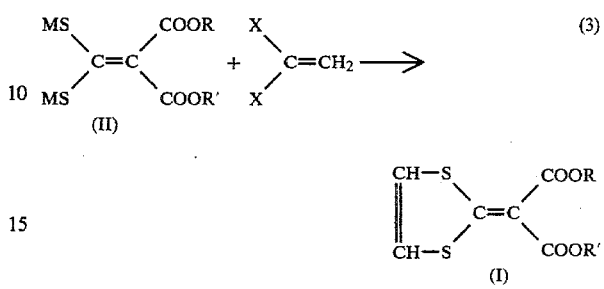

In this equation, M is alkali metal or ammonium, and X, R, and R' are as defined above.

Dialkyloxy carbonyketene dimercaptides represented by formula (II) can be synthesized by the known reaction (4):

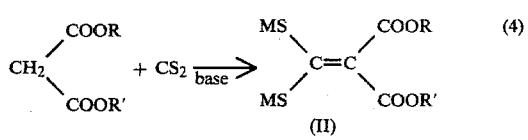

In this equation, R, R', and M are as defined above.

The base ions represented by M in a ketene mercaptide used in this invention, of formula (II) come from the base material used in the reaction of a dialkyl malonate with carbon disulfide, as is obvious from the reaction path of equation (4) schematically shown above. While any base material having reactivity toward a 1,1-dihalogenoethylene can be used in this invention, typical examples of the mercaptan salts are dipotassium salt and disodium salt in the formula (II). Besides these salts, diammonium salt can be used in the process of this invention.

The ester moieties of a compound represented by formula (II) come from the dialkyl malonate used in reaction (4) given above. In this case, the two lower alkyls may be the same or different. Both the lower alkyls include methyl, ethyl, n-propyl, isopropyl, n-butyl, isobutyl, sec-butyl, and t-butyl. Consequently, the compounds represented by formula (II) include the ketene mercaptides derived from the following malonates: dimethyl malonate, diisopropyl malonate, diethyl malonate, di-n-propyl malonate, diallyl malonate, di-n-butyl malonate, diisobutyl malonate, di-tert-butyl malonate, di-sec-butyl malonate, methyl ethyl malonate, methyl isopropyl malonate, methyl n-propyl malonate, ethyl isopropyl malonate, methyl isobutyl malonate, ethyl n-butyl malonate. A typical one of these malonates is diisopropyl malonate, and consequently typical dialkloxycarbonylketene dimercaptides of formula (II) include the following compounds:

Diisopropoxycarbonylketene disodium mercaptide

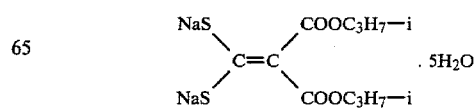

[pale yellow crystal; m.p. 183° C. or more (yellowing)]
Diisopropoxycarbonylketene dipotassium mercaptide

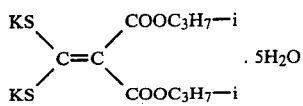

[pale yellow crystal; discolors at 102°–109° C. while foaming; decomposes into black matter at 300° C. or more]

1,1-Dichloroethylene to be used in this invention include 1,1-dichloroethylene and 1,1-dibromoethylene, but the use of the former is more advantageous.

Process (3) of this invention can be accomplished by reacting a ketene mercaptide represented by formula (II) and a 1,1-dihalogenoethylene. This reaction is an equimolar one, but either of reactants may also be used in excess; for example, a 1,1-dihalogenoethylene is used in an amount ratio of 1 to 8 moles, preferably 1 to 3 moles, per mole of the mercaptide used.

This reaction is carried out in a solvent not inhibiting the reaction; preferably in a polar solvent such as, for example, dimethylsulfoxide, N-methylpyrrolidone, dimethylformamide, dimethylacetamide, hexamethylphosphoramide, Sulforane (tetrahdrothiophen-1,1-dioxide), or the like, of which dimethylsulfoxide is most preferable.

This reaction in this invention can also be carried out in a mixture of water-polar solvent because the above solvents, even if they are mixed with water, have enough solvent power.

The reaction temperature can be selected suitably from within the range of about 10° C. to the boiling region of the solvent used. Usually, appropriate reaction temperature lies between room temperation and about 80° C., and preferably is 50° C. to 80° C.

After completion of the reaction, the object matter can be isolated according to a usual separation method; for instance, the object matter can be obtained by extracting it from the reaction mixture in a suitable solvent, followed by a suitable method to remove the solvent.

Meanwhile, it has been found that the above ketene mercaptide which has been obtained as a reaction mixture on synthesis can be used as it is for the ring closure reaction. That is, it can be used without being isolated from the reaction mixture. This method will be illustrated hereinbelow.

When a dialkyl malonate is reacted with carbon disulfide in the presence of a base, the corresponding dialkyloxycarbonylketene dimercaptide can be obtained in the reaction mixture nearly quantitatively. Said ketene dimercaptide can also be obtained in an alkali-water solvent [Japanese patent application Laid-open Nos. 99110 (1973) and 24265 (1975)]or in a polar solvent [Japanese patent application Laid-open No. 13174 (1974)].

Thus, this invention also provides a process for producing 1,3-dithiol-2-ylidene malonates by reacting dialkyl malonates, in the presence of a base, with carbon disulfide and successively with a 1,1-dihalogenoethylene. This reaction is conveniently carried out by use of a polar solvent or a mixture thereof with water. The water in this case is generally brought from the aqueous solution of the base. Sodium hydroxide and potassium hydroxide are typical examples of the preferred base, and ammonia can also be used, but potassium hydroxide is particularly preferable. The amount of the base used may be about 2 to 3 moles per mole of the dialkyl malonate used. The reaction of dialkyl malonates with carbon disulfide is desirable to start at a temperature not exceeding 30° C. since it is exothermic, and thereafter it may be carried out at a temperature of about 50° to 80° C. Carbon disulfide is desirable to use in an amount ratio of about 0.9 to about 1.2 moles per mole of the dialkyl malonate used. The process of this invention involves the following embodiments, but is not limited thereto:

(1) Required amounts of a dialkyl malonate, carbon disulfide, and of a 1,1-dihalogenoethylene are put together with a polar solvent in a vessel, and a required amount of an aqueous solution of a base is added thereto, whereby reaction is carried out.

(2) Required amounts of a dialkyl malonate and of carbon disulfide are put in a polar solvent, and an aqueous solution of a base and subsequently a 1,1-dihalogenoethylene alone or dissolved in a polar solvent are added thereto, whereby reaction is carried out.

(3) To a mixture of required amounts of a dialkyl malonate and of carbon disulfide, an aqueous solution of a base and subsequently a polar solvent containing a required amount of 1,1-dihalogenoethylene are added thereto, whereby reaction is carried out.

(4) A resulting mixture of the reaction of a dialkyl malonate with carbon disulfide and an aqueous solution of a base is added to a polar solvent containing a required amount of a 1,1-dihalogenoethylene, whereby reaction is carried out.

After completion of the reaction, the object matter can be isolated by a method mentioned above.

The following compounds are typical examples that can be synthesized according to the process of this invention. These compounds are shown in terms of R and R' in the formula:

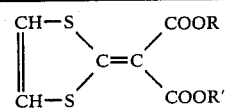

| No. | R | R' | Melting point or refrative index |
|---|---|---|---|
| 1 | $CH_3$ | $CH_3$ | m.p. 134.5–135° C. |
| 2 | $C_2H_5$ | $C_2H_5$ | m.p. 113° C. |
| 3 | $i-C_3H_7$ | $i-C_3H_7$ | m.p. 60.5° C. |
| 4 | $n-C_3H_7$ | $n-C_3H_7$ | m.p. 73–75° C. |
| 5 | $i-C_4H_9$ | $i-C_4H_9$ | m.p. 76–78° C. |
| 6 | $n-C_4H_9$ | $n-C_4H_9$ | m.p. 55–57° C. |
| 7 | $C_2H_5$ | $i-C_3H_7$ | m.p. 57–58° C. |
| 8 | $CH_3$ | $i-C_4H_9$ | $n_D^{20}$ 1.5928 |

The following examples illustrate the process of this invention, which is, however, not limited to these examples.

EXAMPLE 1

Diisopropyl malonate (18.8 g, 0.1 mol) and carbon disulfide (7.6 g, 0.1 mol) were dissolved in 200 ml of dimethyl sulfoxide. Dropping thereto a 35% potassium hydroxide aqueous solution (40 g, 0.25 mol KOH) at 13°–17° C. gave a pale yellowish red solution containing diisopropoxycarbonylketene dipotassium mercaptide. After addition of 1,1-dichloroethylene (14.4 g, 0.15 mol) to this solution at 20° C., the temperature was gradually raised to 70° C. to carry out reaction for 30 minutes.

Then, the resulting mixture was poured into ice-water, and extracted with benzene. Drying of the extract over anhydrous magnesium sulfate, distillation to remove benzene, and recrystallization from ligroin gave 21.6 g of the object matter, diisopropyl 1,3-dithiol-2-ylidene malonate, m.p. 60.5° C., yield 75%.

EXAMPLE 2

Diisopropyl malonate (18.8 g, 0.1 mol), carbon disulfide (7.6 g, 0.1 mol), and 1,1-dichloroethylene (14.4 g, 0.15 mol) were dissolved in 100 ml of dimethylsulfoxide, and a 35% potassium hydroxide aqueous solution (40 g, 0.25 mol ROH) was dropped thereto. Reaction was carried out for 30 minutes keeping the reaction temperature at about 60° C. by controlling the temperature rise due to reaction heat. The resulting mixture was poured into ice-water and extracted with benzene. Drying of the extract over anhydrous magnesium sulfate, distillation to remove benzene, and recrystallization from n-hexane gave 24.2 g of the object matter; m.p. 60.5° C., yield 84%.

EXAMPLE 3

A 45% potassium hydroxide aqueous solution (31 g, 0.25 mol KOH) was slowly added dropwise to a mixture of diisopropyl malonate (18.8 g, 0.1 mol) with carbon disulfide (7.6 g, 0.1 mol) while cooling the reaction mixture to a temperature not exceeding 20° C. A pale yellow aqueous solution of diisopropoxy carbonylketene mercaptide was obtained by stirring the mixture for 10 minutes after completion of the dropping. This solution was dropped at 20° C. to the solution consisting of 1,1-dichloroethylene (19.2 g, 0.2 mol) and 200 ml of dimethylsulfoxide. Reaction was continued at 60° C. for further 30 minutes after completion of the dropping, and then the resulting mixture was poured into ice-water and extracted with benzene. Drying of the extract over anhydrous magnesium sulfate, distillation to remove benzene, and recrystallization from n-hexane gave 20.7 g of the object matter; m.p. 60.5° C., yield 71.9%.

EXAMPLE 4

A pale yellow aqueous solution of diisopropoxycarbonylketene dipotassium mercaptide was obtained by dropping a 48.5% potassium hydroxide aqueous solution (243 g, 2.1 mol KOH) to a mixture of diisopropyl malonate (189 g, 1.0 mol) with carbon disulfide (76 g, 1.0 mol) while keeping the temperature not exceeding 20° C. This solution was dropped at a temperature not exceeding 20° C. to the solution consisting of 1,1-dichloroethylene (97 g, 1.0 mol) and 2.0 l of dimethylsulfoxide. After completion of the dropping, the reaction mixture was left at room temperature for 30 minutes with stirring continued, where the reaction temperature rose to nearly 25° C. by gradual heat evolution. Then, the mixture was heated to 75° C. for 15 minutes to complete reaction. The resulting mixture was cooled to room temperature and filtered to remove the precipitated crystals. The filtrate, after addition of 150 ml of water, extracted twice with 2 l each of benzene. Washing of the benzene layer with water, followed by distillation to remove benzene, gave 251 g of the object matter; m.p. 60.5° C., yield 87%.

EXAMPLE 5

A pale yellow crystals of diisoproxycarbonylketene dipotassium mercaptide (43 g, 0.1 mol) was added to the solution consisting of 1,1-dichloroethylene (9.7 g, 0.1 mol) and 200 ml of dimethylsulfoxide. After stirred at room temperature for 30 minutes, the reaction mixture was heated to react at 75° C. for 15 minutes. The resulting mixture was cooled to room temperature, admixed with ice-water to dissolve the precipitated salt, and extracted twice with 300 ml each of cyclohexane. Washing of the extract with water, followed by distillation to remove the solvent, gave 20.3 g of the object matter, m.p. 60.5° C., yield 70.5%.

In a similar manner, 17.6 g of the object matter was obtained from diisopropoxycarbonylketene disodium mercaptide and 1,1-dichloroethylene; m.p. 60.5° C., yield 61%.

EXAMPLE 6

Diisopropyl malonate (18.8 g, 0.1 mol), carbon disulfide (7.6 g, 0.1 mol), and 1,1-dichloroethylene (19.4 g, 0.2 mol) were dissolved in 300 ml of N,N-dimethylacetamide, and a 48.5% potassium hydroxide aqueous solution (26.6 g, 0.23 mol KOH) was dropped thereto at 20°-30° C. Thereafter, the mixture was heated slowly to react at 75° C. for 20 minutes. The resulting mixture was cooled to room temperature, admixed ice-water to dissolve the precipitated salt, and extracted with 1 l of benzene. Washing of the extract with water, followed by distillation to remove the solvent, gave 12.5 g of the object matter; m.p. 60.5° C., yield 43.4%.

In the same manner as the above except for using dimethylformamide in place of N,N-dimethylacetamide, 13.6 g of the object matter was obtained; m.p. 60.5° C., yield 47.2%.

What is claimed is:

1. A process for producing 1,3-dithol-2-ylidene malonic acid dialkyl esters which is characterized by reacting a dialkyloxycarbonylketene dimercaptide with a 1,1-dihalogenoethylene.

2. A process of claim 1, wherein said reaction is carried out in a polar solvent.

3. A process of claim 2, wherein said polar solvent is dimethylsulfoxide.

4. A process for producing 1,3-dithiol-2-ylidene malonic acid dialkyl esters which is characterized by reacting a malonic acid dialkyl ester, in the presence of a base, with carbon disulfide and successively with a 1,1-dihalogenoethylene.

5. A process of claim 4, wherein said reaction is carried out in a polar solvent.

6. A process of claim 5, wherein said polar solvent is dimethylsulfoxide.

7. A process of claim 5, wherein said malonic acid dialkyl ester is diisopropyl malonate.

* * * * *